United States Patent [19]

Bull et al.

[11] Patent Number: 4,789,671

[45] Date of Patent: Dec. 6, 1988

[54] 14,17β-ETHANO-14β-ESTRATRIENES AND ESTRATETRAENES, PROCESS FOR THEIR PRODUCTION, AND PHARMACEUTICAL PREPARATIONS CONTAINING THEM

[75] Inventors: James R. Bull; Russell I. Thomson, both of Pretoria, South Africa; Henry Laurent, Berlin; Helmut Schroeder, Berlin; Rudolf Wiechert, Berlin, all of Fed. Rep. of Germany

[73] Assignee: Schering Aktiengesellschaft, Berlin and Bergkaman, Fed. Rep. of Germany

[21] Appl. No.: 20,009

[22] Filed: Feb. 27, 1987

[30] Foreign Application Priority Data

Aug. 20, 1986 [DE] Fed. Rep. of Germany ....... 3628189

[51] Int. Cl.$^4$ ........................... A61K 31/56; C07J 1/00
[52] U.S. Cl. .................................. 514/182; 260/397.5
[58] Field of Search ..................... 514/182; 260/397.5

[56] References Cited

PUBLICATIONS

Bull et al., J. Chem. Soc., Chem. Commun, 1986, pp. 451–453.
Bischofberger et al., Tetrahedron, vol. 41, No. 2, 1985, pp. 365–374.
Bull et al., J. Chem. Soc. Perkin Trans. I 1983, pp. 2723–2727.
Groen et al., Tetrahedron Ltrs., vol. 23, No. 35, pp. 3611–3614, 1982.
Chemical Abstracts, Band 105, No. 17, Oct. 27, 1986, J. R. Bull et al., "Cycloaddition . . . " J. Chem. Soc. 1986 (VI), 451–453.
Journal of Medicinal Chemistry, Band 16, No. 3, Mar. 1973, Solo et al., "Ring D Bridged Steroid Analogs . . . ", 270–273.

*Primary Examiner*—Leonard Schenkman
*Assistant Examiner*—Joseph A. Lipovsky
*Attorney, Agent, or Firm*—Millen & White

[57] ABSTRACT

14,17β-ethano-14β-estratriene and estratetraene of Formula I

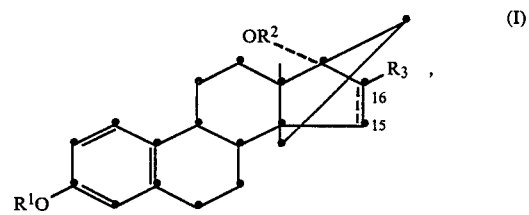

wherein
$R^1$ is a hydrogen atom, a methyl or an acyl group of a monocarboxylic acid of 1–12 carbon atoms,
$R^2$ is a hydrogen atom or an acyl group of a monocarboxylic acid of 1–12 carbon atoms,
$R^3$ is a hydrogen atom or a methyl group, and

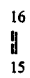

is a single or double C—C-bond
show strong estrogenic activity.

27 Claims, No Drawings

14,17β-ETHANO-14β-ESTRATRIENES AND ESTRATETRAENES, PROCESS FOR THEIR PRODUCTION, AND PHARMACEUTICAL PREPARATIONS CONTAINING THEM

DETAILED DESCRIPTION OF THE INVENTION

This invention relates to 14,17β-Ethano-14β-estratrienes and estratetraenes of Formula I

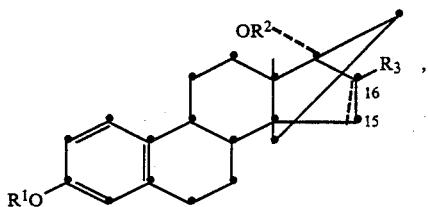

wherein
$R^1$ is a hydrogen atom, a methyl or an acyl group of a monocarboxylic acid of 1-12 carbon atoms,
$R^2$ is a hydrogen atom or an acyl group of a monocarboxylic acid of 1-12 carbon atoms,
$R^3$ is a hydrogen atom or a methyl group, and

is a single or double C—C-bond.

The ester residues $R_1$ and $R_2$ in Formula I can be derived from an aliphatic, cycloaliphatic-aliphatic or aromatic monocarboxylic acid. The cyclic moiety has 3-7 C-atoms. Preferred ester residues $R^1$ and $R^2$ are those of acetic acid, propionic acid, butyric acid, isobutyric acid, pivalic acid, capronic acid, enanthic acid, octanoic and decanoic acid, furthermore β-cyclopentylpropionic acid and benzoic acid. Thus, preferred acyl groups are hydrocarbon in nature; aromatic such groups are generally of 6-10 ring atoms (e.g., phenyl or 1- or 2-naphthyl). Preferred groups include alkanoyl, cycloalkylalkanoyl and benzoyl.

It has been found that these compounds show a strong binding to the estrogen receptor and in the Allen-Doisy test on estrogen action after sub-cutaneous and oral application are more strongly estrogen-active than ethynyl estradiol.

In the Allen-Doisy test, an evaluation is taken from vaginal smears in ovariectomized rats on the 3rd, 4th, 5th and 6th days after a single application of the test substance. The following cycle stages are distinguished:
1 = Dioestrus (leucocytes and epithelial cells containing nuclei)
2 = Prooestrus (epithelial cells containing nuclei)
3 = Oestrus (horny lumps without nuclei)
4 = Metoestrus (horny lumps without nuclei, leucocytes or epithelial cells).

Substances with estrogen activity, after oral or subcutaneous application, lead to the proliferation of vaginal epithelia and to the hardening of the superficial cell layers.

That quantity of an estrogen is regarded as the threshold value by which 50% of the animals reach stage 3.

After application of, for example 10 μg of 14,17β-ethano-14β-estra-1,3,5(10)-triene-3,17α-diol per os, stage 3 is reached by 50% of the animals, while in the control group with 10 μg of ethinyl estradiol, a complete stage 3 is not recognizable in any rat.

It is surprising that the compounds according to the invention which contain no 17α-ethynyl group, are more active orally than ethinyl estradiol. Ethinyl estradiol is now the most commonly used estrogen for oral treatment.

The invention is thus concerned also with the use of compounds of general Formula I for the treatment of symptoms of estrogen deficiency and for fertility control in women.

Compounds of this invention are also useful as intermediates as described in J. Chem. Soc., Chem. Commun., 1986, 451-453, March, 1986; Tetrahedron, 1985, 41, 365, J. Chem. Soc., Perkin Trans. 1, 1983, 2723; and Tetrahedron Lett., 1982, 23, 3611, all of which are entirely incorporated by reference herein.

The compounds according to the invention can be formulated and used in the same way as ethinyl estradiol. They can be formulated in the conventional manner for pharmaceuticals with the usual additives, vehicles and taste correctors, according to well known methods in pharmacy. For oral application, tablets, plain or sugar-coated, capsules, pills, suspensions or solutions are particularly used. For parenteral application, oily solutions, such as for example, sesame oil or castor oil solutions are used, which, if desired, can contain as an additive, a diluent such as, for example, benzyl benzoate or benzyl alcohol.

The concentration of active material in the pharmaceutical compositions depends on the application form and the nature of its use. Thus, for example, capsules or tablets for the treatment of estrogen deficiency symptoms contain 0.001 to 0.05 mg of active material (administered, e.g., once daily), oily solutions for intramuscular injection some 50 to 100 mg of active material per 1 ml and vaginal ointments some 0.1 to 10 mg per 100 ml of ointment. For contraception in women, the estrogen according to the invention can be used in combination with gestagens. Tablets, plain or sugar-coated, to be taken daily preferably contain 0.003 to 0.05 mg of the estrogen according to the invention and 0.05 to 0.5 mg of a gestagen.

For example, in a preferred mode, the compound of example 17 is used in an oily solution as a depot medication. A 1 ml intramuscular injection of this formulation is effective for 2-3 weeks.

The compounds according to the invention can be used to treat symptoms of estrogen deficiency in women, such as for example, amenorrhoea, dysmenorrhoea, sterility, frigidity, endometriosis, colpitis and menopausal symptoms.

The preparation of the compounds of general Formula I is carried out starting with the steroidal phenyl sulfon of Formula II

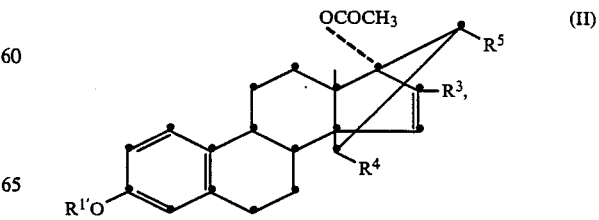

wherein $R^1$ is a methyl or an acetyl group;
$R^3$ is a hydrogen atom or a methyl group;
$R^4$ is hydrogen and $R^5$ is phenylsulfphonyl,
when $R^3$ is hydrogen;
and one of $R^4$ or $R^5$ is phenylsulphonyl and the other is hydrogen,
when $R^3$ is methyl;
by reductive removal of the phenylsulphonyl group with amalgam or Raney nickel and, if desired, by subsequent hydrogenation of the $\Delta^{15}$double bond and, if desired, by subsequent cleavage of the 3-methyl ether or saponification of the acetoxy groups and subsequent optional esterification of the phenolic and tertiary hydroxy groups and subsequent optional partial saponification of the phenolic esters.

Removal of the phenylsulphonyl group takes place conventionally with a reducing agent. Preferred reducing agents are amalgams, especially sodium amalgam, and Raney nickel.

The subsequent hydrogenation can be carried out in known manner. The hydrogenation preferably takes place in the presence of a noble metal catalyst on an inert carrier.

The subsequent optional cleavage of a 3-methyl ether can be carried out according to the usual methods for cleaving a steroid ether. Thus, the cleavage of the 3-methyl ether can be carried out, for example, with a Lewis acid in an inert solvent at its boiling point. Suitable Lewis acids are, for example, boron trifluoride etherate or diisobutylaluminum hydrid (DIBAH). Suitable solvents include benzene, toluene, tetrahydrofurane and dioxane.

The saponification of the acetoxy group can be carried out in known manner. For example, the saponification can be carried out with bases in an aqueous-alcoholic solution, such as potassium carbonate in an aqueous-methanolic solution.

For subsequent optional esterification of the phenolic and tertiary hydroxy groups, processes usually used in steroid chemistry for esterification can be used. For example, the reaction with the corresponding monocarboxylic acid or a derivative, especially the anhydride or chloride of the monocarboxylic acid, in the presence of stronger acids, for example, trifluoroacetic acid, perchloric acid or p-toluene sulphonic acid, at room temperature or somewhat higher temperature, or the reaction with anhydride or chloride in the presence of a tertiary amine at about 20°-80° C. may be mentioned.

If pyridine and 4-dimethylaminopyridine are used together as the tertiary amine, the esterification can preferably be carried out at room temperature.

The compounds of Formula II can be synthesized by reaction of the known 17-acetoxy-3-methoxyestra-1,3,5(10),14,16-pentaene (Steroids 1973, 22, 107) or estra-1,3,5(10),14,16-pentaene-3,17-diol diacetate (J. Org. Chem., 1972, 37, 2127) or 3-methoxy-16-methylestra-1,3,5(10),14,16-pentaene-17-ol acetate with phenyl vinyl sulphone.

3-Methoxy-16-methyl-estra-1,3,5(10),14,16-pentaene-17-ol acetate can be synthesized starting with 3-methoxy-16-methyl-estra-1,3,5(10),15-tetraene-17-one (German Offenlegungsschrift No. 3023568) in the described manner.

Similar reactions of an En with a Dien are reported in J. Org. Chem. 1983, 48, 4976 and Steroids 1968, 11, 637.

PREPARATION OF THE STARTING COMPOUNDS (A)

14,17β-Ethano-3-methoxy-2'-phenylsulphonyl-14β-estra-1,3,5(10),15-tetraene-17α-ol acetate A mixture of 4 g of 17-acetoxy-3-methoxyestra-1,3,5(10),14,16-pentaen and 6.23 g of phenyl vinyl sulphone in 15 ml of dry benzene is heated in a sealed tube at 140° C. for 90 hours. The reaction mixture is cooled to room temperature and chromatographed on silica gel using benzene-ethyl acetate (19:1) as eluent. 5.57 g of 14,17β-ethano-3-methoxy-2'-phenylsulphonyl-14β-estra-1,3,5(10),15-tetraene-17α-ol acetate is obtained, which after recrystallisation from benzene-hexan, melts at 180°-181.5° C.

(B)

14,17β-Ethano-2'-phenylsulphonyl-14β-estra-1,3,5(10),15-tetraene-3,17α-diol diacetate A mixture of 1.23 g estra-1,3,5(10),14,16-pentaene-3,17-diol diacetate and 1.77 g of phenyl vinyl sulphone in 4.6 ml of dry benzene is heated in a sealed tube at 140° C. for 90 hours. The reaction mixture is cooled to room temperature and chromatographed on silica gel using benzene-ethyl acetate (19:1) as eluent. 1.5 g 14,17β-ethano-2'-phenylsulphonyl-14β-estra-1,3,5(10),15-tetraene-3,17α-diol diacetate is obtained, which after recrystallisation from acetone-hexane melts at 196°-197° C.

(C) Mixture of 14,17β-Ethano-3-methoxy-16-methyl-2'-phenyl-sulphonyl-14β-estra-1,3,5(10),15-tetraene-17α-ol acetate and 14,17β-Ethano-3-methoxy-16-methyl-1'-phenylsulphonyl-14β-estra-1,3,5(10),15-tetraene-17α-ol acetate A solution of 20.0 g of 3-methoxy-16-methylestra-1,3,5(10),15-tetraene-17-one in 400 ml of isopropenyl acetate and 80 ml of acetic anhydride is prepared. 6.0 g of p-toluene sulphonic acid is then added and the mixture is stirred for 20 hours at 100° C. The cooled reaction mixture is poured into ice-water and stirred for 1.5 hours while neutralising with solid NaHCO$_3$. This mixture is extracted with benzene three times. The combined benzene layers are washed twice with water, dried with MgSO$_4$ and concentrated to give 23.5 g of a brown crystalline residue. Filtration chromatography on silica and elution with benzene-ethyl acetate (50:1) afforded 21.8 g of the dienyl acetate. Recrystallisation from ethyl acetate-methanol yields 19.81 g of 3-methoxy-16-methyl-estra-1,3,5(10),14,16-pentaene-17-ol acetate (dienyl acetate).

A solution of 19.81 g of dienyl acetate and 10.34 g of phenyl vinyl sulphone in 35 ml of dry xylene is placed into a pressure ampoule under inert conditions and heated at 140° C. for 120 hours. The reaction is cooled to room temperature and chromatographed on silica gel using benzene-ethyl acetate (1:1). 22.27 g of a 1:1-mixture of 14,17β-ethano-3-methoxy-16-methyl-2'-phenyl-sulphonyl-14β-estra-1,3,5(10),15-tetraene-17α-ol acetate and 14,17β-ethano-3-methoxy-16-methyl-1'-phenylsulphonyl-14β-estra-1,3,5(10),15-tetraene-17α-ol acetate is obtained.

EXAMPLES

Example 1

14,17β-Ethano-3-methoxy-14β-estra-1,3,5(10),15-tetraene-17α-ol acetate

At −20° C. under an argon atmosphere 31.5 g of sodium amalgam (6%) is added to a stirred solution of 2 g of 14,17β-ethano-3-methoxy-2'-phenylsulphonyl-14β-estra-1,3,5(10),15-tetraene-17α-ol acetate and 2.33 g of anhydrous disodium hydrogen phosphate in a mixture of 40 ml of dry methanol and 10 ml of dry tetrahydrofuran. The reaction mixture is stirred at −20° C. for 3 hours and then quenched by the addition of 40 ml of water. The solution is decanted and the amalgam washed successively with water and ethyl acetate. The aqueous layer is separated and extracted with ethyl acetate. The combined organic layers are washed once with brine, dried over sodium sulphate and concentrated in vacuo to give 1.42 g of crude product. This crude product is taken up in 15 ml of acetic anhydride and 50 mg of p-toluene-sulphonic acid is added. This reaction mixture is stirred at room temperature for 16 hours and then quenched by the addition of ice and solid sodium hydrogen carbonate. The aqueous layer is separated and extracted with benzene and the combined organic layers are washed with saturated aqueous sodium hydrogen carbonate and brine, dried over sodium sulphate and concentrated in vacuo to give a crystalline residue which is recrystallised from methanol to give 1.19 g of 14,17β-ethano-3-methoxy-14β-estra-1,3,5(10),15-tetraene-17α-ol acetate, m.p. 119°–121° C.

Example 2

14,17β-Ethano-14β-estra-1,3,5(10),15-tetraene-3,17α-diol 20 g of Sodium amalgam (6%) is added to a stirred solution of 1.05 g of 14,17β-ethano-2'-phenylsulphonyl-14β-estra-1,3,5(10),15-tetraene-3,17α-diol diacetate and 1.14 g of anhydrous disodium hydrogen phosphate in 20 ml of dry methanol and 5 ml of dry tetrahydrofuran at −20° C. under an argon atmosphere. The reaction mixture is stirred at −20° C. for 2 hours and then quenched by the addition of 20 ml of water. The solution is decanted and the amalgam washed successively with water and ethyl acetate. The aqueous layer is separated and extracted with ethyl acetate. The combined organic layers are washed once with brine, dried over sodium sulphate and concentrated in vacuo to give 0.69 g of crude product. This crude product is dissolved in 5 ml of tetrahydrofuran and 10 ml of methanolic potassium hydroxide (1M) is added to this solution. After stirring for 2 hours, the reaction mixture is poured into 100 ml of water. The aqueous layer is acidified with dilute hydrochloric acid to a pH of 5 and then extracted with ethyl acetate. The combined organic layers are washed once with brine, dried over sodium sulphate and concentrated in vacuo to give a crystalline residue which is recrystallised from benzene-ethyl acetate to give 0.56 g of 14,17β-ethano-14β-estra-1,3,5(10),15-tetraene-3,17α-diol, m.p. 228°–229° C.

Example 3

14,17β-Ethano-14β-estra-1,3,5(10),15-tetraene-3,17α-diol diacetate 1.25 g of 14,17β-ethano-14β-estra-1,3,5(10),15-tetraene-3,17α-diol is taken up in 20 ml of acetic anhydride and a catalytic amount of p-toluenesulphonic acid is added. The reaction mixture is stirred at room temperature for 16 hours and then quenched by the addition of ice and solid sodium hydrogen carbonate. The aqueous layer is separated and extracted with benzene and the combined organic layers are washed with saturated aqueous sodium hydrogen carbonate and brine, dried over sodium sulphate and concentrated in vacuo to give 2.6 g of crude product. By chromatography on silica gel using benzyl-ethyl acetate (19:1) as eluent 1.48 g of 14,17β-ethano-14β-estra-1,3,5(10),15-tetraene-3,17α-diol diacetate is obtained, m.p. 102'–103.5° C.

Example 4

14,17β-Ethano-14β-estra-1,3,5(10),15-tetraene-3,17α-dioldivalerate

The esterification of 14,17β-ethano-14β-estra-1,3,5(10),15-tetraene-3,17α-diol with valeric anhydride in the presence of p-toluenesulphonic acid under the conditions described in Example 3, yields 14,17β-ethano-14β-estra-1,3,5(10),15-tetraene-3,17α-diol divalerate.

Example 5

14,17β-Ethano-3-methoxy-14β-estra-1,3,5(10),15-tetraene-17α-ol 100 ml of Methanolic potassium hydroxide (1M) is added to a stirred solution of the 5.23 g of 14,17β-ethano-3-methoxy-14β-estra-1,3,5(10),15-tetraene-17α-ol acetate in 30 ml of tetrahydrofuran at room temperature under argon. After stirring for 1 hour, the reaction mixture is poured into 200 ml of water. The aqueous layer is acidified with dilute hydrochloric acid to a pH of 5 and then extracted with ethyl acetate. The combined organic layers are washed once with brine, dried over sodium sulphate and concentrated in vacuo to give a crystalline residue which is recrystallised from benzene-hexane to give 4.42 g of 14,17β-ethano-3-methoxy-14β-estra-1,3,5(10),15-tetraene-17α-ol, m.p. 151°–152° C.

Example 6

14,17β-Ethano-3-methoxy-14β-estra-1,3,5(10)-triene-17α-ol

A solution of 61.2 mg of 14,17β-ethano-3-methoxy-14β-estra-1,3,5(10),15-tetraene-17α-ol in 6 ml of ethyl acetate is hydrogenated in the presence of 20 mg of palladium on charcoal (5%) at room temperature under normal pressure. When the take up of hydrogen ceases, the catalyst is filtered off. The catalyst is washed with ethyl acetate, and the combined organic phases are evaporated under reduced pressure. After filtration through a silica gel column using a mixture of benzene and ethyl acetate (9:1), 60 mg of 14,17β-ethano-3-methoxy-14β-estra-1,3,5(10)-triene-17α-ol is obtained, which after recrystallisation from methanol, melts at 120.5°–121° C.

Example 7

14,17β-Ethano-14β-estra-1,3,5(10)-triene-3,17α-diol 1.2 ml of a 1.2 molar solution of diisobutylaluminium hydride in toluene is added to a solution of 128 mg of 14,17β-ethano-3-methoxy-14β-estra-1,3,5(10)-triene-17α-ol in 6 ml of toluene, with stirring and under an inert protective atmosphere (argon). After heating at reflux for 24 hours, the reaction mixture is cooled and diluted with 5 ml of 10% hydrochloric acid. The aqueous phase is separated and extracted three times with 25 ml of ethyl acetate. The organic phases are combined and washed with aqueous sodium chloride, dried over sodium sulphate and evaporated under reduced pressure. After chromatography on silica gel using chloroform/methanol (19:1), 111 mg of 14,17β-ethano-14β-estra-1,3,5(10)-triene-3,17α-diol, is obtained, which, after recrystallizing from chloroform/methanol, melts at 240°–241° C.

Example 8

14,17β-Ethano-14β-estra-1,3,5(10)-triene,3,17α-diold-iacetate 10 mg of p-toluene-sulphonic acid is added to a solution of 75 mg of 14,17β-ethano-14β-estra-1,3,5(10)-triene-3,17α-diol in 1 ml of acetic anhydride. The reaction mixture is stirred for 16 hours at room temperature, then ice-water and sodium bicarbonate are added and the mixture extracted with dichloromethane. The organic phase is washed with water, dried over sodium sulphate and evaporated under reduced pressure. The residue is recrystallized from acetone/hexane.

Yield: 72 mg of 14,17β-ethano-14β-estra-1,3,5(10)-triene-3,17α-diol diacetate.

Example 9

14,17β-Ethano-3-methoxy-14β-estra-1,3,5(10)-triene-17α-ol-acetate 20 mg of 4-dimethylaminopyridine is added to a solution of 50 mg of 14,17β-ethano-3-methoxy-14β-estra-1,3,5(10)-triene-17α-ol in a mixture of 0.25 ml of acetic anhydride and 0.5 ml of pyridine, and heated for 3 hours at 80° C. After cooling, 10 ml of water is added, the product which precipitates is filtered off and dissolved in dichloromethane. The solution is washed with water, dried over sodium sulphate and evaporated under reduced pressure. The residue is recrystallized from acetone/hexane, yielding 46 mg of 14,17β-ethano-3-methoxy-14β-estra-1,3,5(10)-triene-17α-ol acetate.

Example 10

14,17β-Ethano-3-methoxy-14β-estra-1,3,5(10)-triene-17α-ol-propionate

Esterification of 14,17β-Ethano-3-methoxy-14β-estra-1,3,5(10)-triene-17α-ol with propionic anhydride, under the conditions set forth in Example 9, yields 14,17β-ethano-3-methoxy-14β-estra-1,3,5(10)-triene-17α-ol propionate.

Example 11

14,17β-Ethano-3-methoxy-14β-estra-1,3,5(10)-triene-17α-ol-hexanoate

Under the conditions set forth in Example 9, 14,17β-ethano-3-methoxy-14β-estra-1,3,5(10)-triene-17α-ol yields with hexanoic anhydride 14,17β-ethano-3-methoxy-14β-estra-1,3,5(10)-triene-17α-ol hexanoate.

Example 12

14,17β-Ethano-3-methoxy-14β-estra-1,3,5(10),15-tetraene-17α-ol butyrate

Esterification of 14,17β-ethano-3-methoxy-14β-estra-1,3,5(10)-15-tetraene-17α-ol with butyric anhydride, yields 14,17β-ethano-3-methoxy-14β-estra-1,3,5(10),15-tetraene-17α-ol butyrate.

Example 13

14,17β-Ethano-14β-estra-1,3,5(10)-triene-3,17α-diol dipropionate

Under the conditions set forth in Example 9, 14,17β-ethano-14β-estra-1,3,5(10)-triene-3,17α-diol yields with propionic anhydride, 14,17β-Ethano-14β-estra-1,3,5(10)-triene-3,17α-diol dipropionate.

Example 14

14,17β-Ethano-14β-estra-1,3,5(10)-triene-3,17α-diol dibutyrate

Under the conditions set forth in Example 9, 14,17β-ethano 14β-estra-1,3,5(10)-triene-3,17α-diol yields with butyric anhydride, 14,17β-Ethano-14β-estra-1,3,5(10)-triene-3,17α-diol dibutyrate.

Example 15

14,17β-Ethano-14β-estra-1,3,5(10)-triene-3,17α-diol diisobutyrate

Under the conditions set forth in Example 9, 14,17β-ethano-14β-estra-1,3,5(10)-triene-3,17α-diol yields with isobutyric anhydride, 14,17β-ethano-14β-estra-1,3,5(10)-triene-3,17α-diol diisobutyrate.

Example 16

14,17β-Ethano-14β-estra-1,3,5(10)-triene-3,17α-diol dihexanoate

Under the conditions set forth in Example 9, 14,17β-ethano-14β-estra-1,3,5(10)-triene-3,17α-diol yields with hexanoic anhydride, 14,17β-ethano-14β-estra-1,3,5(10)-triene-3,17α-diol dihexanoate.

Example 17

14,17β-Ethano-14β-estra-1,3,5(10)-triene-3,17α-diol diundecanoate

Under the conditions set forth in Example 9, 14,17β-ethano-14β-estra-1,3,5(10)-triene-3,17α-diol yields with undecanoic anhydride, 14,17β-ethano-14β-estra-1,3,5(10)-triene-3,17α-diol diundecanoate.

Example 18

14,17β-Ethano-14β-estra-1,3,5(10)-triene-3,17α-diol dibenzoate

Under the conditions set forth in Example 9, 14,17β-ethano-14β-estra-1,3,5(10)-triene-3,17α-diol yields with benzoic anhydride, 14,17β-ethano-14β-estra-1,3,5(10)-triene-3,17α-diol dibenzoate.

Example 19

14,17β-Ethano-14β-estra-1,3,5(10)-triene-3,17α-diol 17-acetate

A mixture of 0.8 g of 14,17β-ethano-14β-estra-1,3,5(10)-triene-3,17α-diol diacetate, 0.8 g of potassium carbonate, 24 ml of methanol and 4 ml of water is refluxed for 48 hours. After filtration and evaporation of the reaction mixture the residue is chromatographed on silica gel using a mixture of benzene and ethyl acetate (9:1). After recrystallisation from methanol, 0.4 g of 14,17β-ethano-14β-estra-1,3,5(10)-triene-3,17α-diol 17-acetate is obtained.

Example 20

14,17β-Ethano-14β-estra-1,3,5(10)-triene-3,17α-diol 17-propionate

Starting with 0.8 g of 14,17β-ethano-14β-estra-1,3,5(10)-triene-3,17α-diol dipropionate, under the conditions described in Example 13, 0.5 g of 14,17β-ethano-14β-estra-1,3,5(10)-triene-3,17α-diol 17-propionate is obtained.

Example 21

14,17β-Ethano-3-methoxy-16-methyl-14β-estra-1,3,5(10),15-tetraene-17α-ol

A solution of the mixture of 22.27 g 14,17β-ethano-3-methoxy-16-methyl-2'-phenylsulphonyl-14β-estra-1,3,5(10),15-tetraene-17α-ol acetate and 14,17β-ethano-3-methoxy-16-methyl-1'-phenylsulphonyl-14β-estra-1,3,5(10),15-tetraene-17α-ol acetate in 80 ml of anhydrous tetrahydrofuran and 320 ml of dry methanol is prepared. 31.24 g of disodium hydrogenphosphate (dried in high vacuum at 100° C. for 3 hours) is then added and the mixture is cooled with ice-water. 112 g of sodium amalgam (6%) is added and the mixture is stirred vigorously for 4 hours at 0° C., and 16 hours at room temperature. The reaction mixture is then quenched with 50 ml of water and concentrated in vacuo to about one-third of its volume. The residue is diluted with 300 ml of water, decanted and extracted with chloroform. The chloroform phase is washed once with water, dried with MgSO₄ and concentrated to give 13.0 g of a yellow solid. Chromatography on silica and elution with benzene-ethyl acetate (19:1) yields 11.5 g of 14,17β-ethano-3-methoxy-16-methyl-14β-estra-1,3,5(10),15-tetraene-17α-ol, m.p. 147°–149° C.

Example 22

14,17β-Ethano-16-methyl-14β-estra-1,3,5(10),15-tetraene-3,17α-diol 1,3 ml of diisobutylaluminium hydride in toluene (1,2M) is added to 0.13 g of 14,17β-ethano-3-methoxy-16-methyl-14β-estra-1,3,5(10),15-tetraene-17α-ol in 6 ml of dry benzene, and the mixture is refluxed under nitrogen. After 48 hours, further 0,3 ml of reagent is added, and refluxing is continued for 72 hours. The reaction mixture is quenched with hydrochloric acid (5%), ethyl acetate is added, and the organic layer is separated, dried (MgSO₄), and concentrated. The residue is filtered through silica gel with ethyl acetate-chloroform (1:10) to give 0.10 g of 14,17β-ethano-16-methyl-14β-estra-1,3,5(10),15-tetraene-3,17α-diol, m.p. 197°–203° C.

Example 23

0.003 g of 14,17β-ethano-14β-estra-1,3,5(10)-triene-3,17α-diol and 209.997 g of lactose are mixed homogeneously and 210 mg of this mixture is filled into each size 3 hard gelatine capsule.

Example 24

0.010 g of 14,17β-ethano-14β-estra-1,3,5(10)-triene-3,17α-diol and 209.990 g of lactose are mixed homogeneously and 210 mg of this mixture is filled into each size 3 hard gelatine capsule.

Example 25

Tablets can be produced in the usual way from the following components:

| | |
|---|---|
| 0.010 mg | 14,17β-ethano-14β-estra-1,3,5(10)-triene-3,17α-diol |
| 0.100 mg | 17α-ethynyl-17β-hydroxy-18-methyl-4-estrene-3-one (Levonorgestrel) |
| 55.290 mg | lactose |
| 24.000 mg | microcrystalline cellulose |
| 0.600 mg | magnesium stearate |
| 80.000 mg | total weight of the tablet. |

Example 26

Tablets can be produced in the usual way from the following components:

| | |
|---|---|
| 0.030 mg | 14,17β-ethano-14β-estra-1,3,5(10)-triene-3,17α-diol |
| 0.075 mg | 17α-ethynyl-17β-hydroxy-18-methyl-4,15-estradiene-3-one (Gestoden) |
| 55.295 mg | lactose |
| 24.000 mg | microcrystalline cellulose |
| 0.600 mg | magnesium stearate |
| 80.000 mg | total weight of the tablet. |

What is claimed is:

1. A 14,17β-ethano-14β-estratriene and estratetraene of Formula I

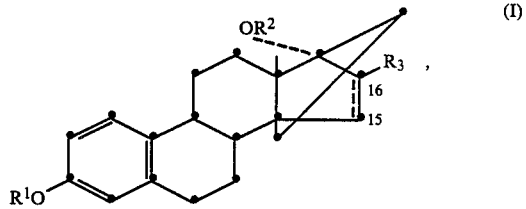

wherein
R¹ is a hydrogen atom, a methyl or an acyl group of a monocarboxylic acid of 1–12 carbon atoms,
R² is a hydrogen atom or an acyl group of a monocarboxylic acid of 1–12 carbon atoms,
R³ is a hydrogen atom or a methyl group, and

is a single or double C—C-bond,
with the proviso that
(a) when R¹ is methyl,

is a double bond and R³ is H, then R² is not acetyl or H;
(b) when R is acyl,

is a double bond and R³ is H, then R² is not acetyl; and
(c) when R¹ is H,

is a double bond and $R^3$ is H, then $R^2$ is not H.

2. A compound of claim 1 which is 14,17β-Ethano-14β-estra-1,3,5(10),15-tetraene-3,17α-diol divalerate.

3. A compound of claim 1 which is 14,17β-Ethano-3-methoxy-14β-estra-1,3,5(10),15-tetraene-17α-ol butyrate.

4. A compound of claim 1, which is 14,17β-Ethano-14β-estra-1,3,5(10)-triene-3,17α-diol.

5. A compound of claim 1, which is 14,17β-Ethano-3-methoxy-14β-estra-1,3,5(10)-triene-17α-ol.

6. A compound of claim 1, which is 14,17β-Ethano-14β-estra-1,3,5(10),triene-3,17α-diol diacetate.

7. A compound of claim 1, which is 14,17β-Ethano-3-methoxy-14β-estra-1,3,5(10)-triene-17α-ol acetate.

8. A compound of claim 1, which is 14,17β-Ethano-3-methoxy-14β-estra-1,3,5(10)-triene-17α-ol propionate.

9. A compound of claim 1, which is 14,17β-Ethano-3-methoxy-14β-estra-1,3,5(10)-triene-17α-ol hexanoate.

10. A compound of claim 1, which is 14,17β-Ethano-14β-estra-1,3,5(10)-triene-3,17α-diol dipropionate.

11. A compound of claim 1, which is 14,17β-Ethano-14β-estra-1,3,5(10)-triene-3,17α-diol dibutyrate.

12. A compound of claim 1, which is 14,17β-Ethano-14β-estra-1,3,5(10)-triene-3,17α-diol diisobutyrate.

13. A compound of claim 1, which is 14,17β-Ethano-14β-estra-1,3,5(10)-triene-3,17α-diol dihexanoate.

14. A compound of claim 1, which is 14,17β-Ethano-14β-estra-1,3,5(10)-triene-3,17α-diol diundecanoate.

15. A compound of claim 1, which is 14,17β-Ethano-14β-estra-1,3,5(10)-triene-3,17α-diol dibenzoate.

16. A compound of claim 1, which is 14,17β-Ethano-14β-estra-1,3,5(10)-triene-3,17α-diol 17-acetate.

17. A compound of claim 1, which is 14,17β-Ethano-14β-estra-1,3,5(10)-triene-3,17α-diol 17-propionate.

18. A compound of claim 1, which is 14,17β-Ethano-3-methoxy-16-methyl-14β-1,3,5(10),15-tetraene-17α-ol.

19. A compound of claim 1, which is 14,17β-Ethano-16-methyl-14β-estra-1,3,5(10),15-tetraene-3,17α-diol.

20. A 14,17β-ethano-14β-estratriene or estratetraene of Formula I

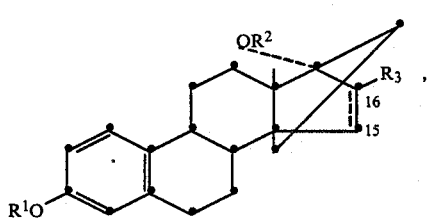

wherein
(a) $R^2$ is methyl, --- is a double bond, $R^3$ is H, and $R^2$ is acetyl or H;
(b) $R^1$ is acetyl, --- is a double bond, $R^3$ is H, and $R^2$ is acetyl; and
(c) $R^1$ is H, --- is a double bond, $R^3$ is H, and $R^2$ is H.

21. A compound of claim 20 which is 14,17β-Ethano-3-methoxy-14β-estra-1,3,5(10),15-tetraene-17α-ol acetate.

22. A compound of claim 20 which is 14,17β-Ethano-14β-estra-1,3,5(10),15-tetraene-3,17α-diol.

23. A compound of claim 20 which is 14,17β-Ethano-14β-estra-1,3,5(10),15-tetraene-3,17α-diol diacetate.

24. A compound of claim 27 which is 14,17β-Ethano-3-methoxy-14β-estra-1,3,5(10),15-tetraene-17α-ol.

25. A pharmaceutical composition comprising an estrogenically effective amount of a compound of general Formula I, in unit dosage form and in admixture with a pharmaceutically acceptable carrier, wherein Formula I is

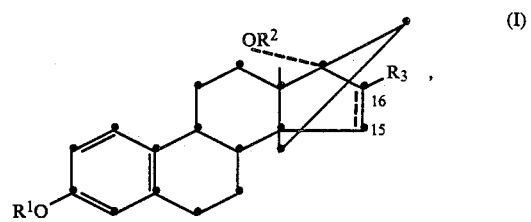

wherein $R^1$ is a hydrogen atom, a methyl or an acyl group of a monocarboxylic acid of 1–12 carbon atoms, $R^2$ is a hydrogen atom or an acyl group of a monocarboxylic acid of 1–12 carbon atoms, $R^3$ is a hydrogen atom or a methyl group, and

is a single or double C—C-bond.

26. A method of treating symptoms of estrogen deficiency or for the control of fertility in women which comprises administering an effective amount of a compound of general Formula I,

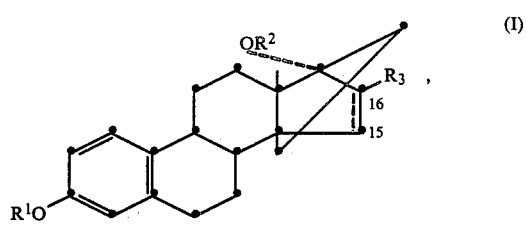

wherein $R^1$ is a hydrogen atom, a methyl or an acyl group of a monocarboxylic acid of 1–12 carbon atoms, $R^2$ is a hydrogen atom or an acyl group of a monocarboxylic acid of 1–12 carbon atoms, $R^3$ is a hydrogen atom or a methyl group, and

is a single or double C—C-bond.

27. A process for the preparation of a compound of general Formula I

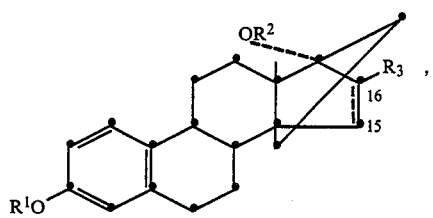 (I)

wherein
R[1] is a hydrogen atom, a methyl or an acyl group of a monocarboxylic acid of 1–12 carbon atoms,
R[2] is a hydrogen atom or an acyl group of a monocarboxylic acid of 1–12 carbon atoms,
R[3] is a hydrogen atom or a methyl group, and --- is a single or double C—C-bond, comprising reductively removing, with amalgam or Raney nickel, the phenylsulphonyl group from a compound of general Formula II

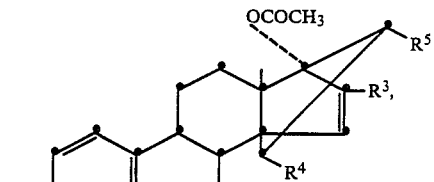 (II)

wherein
R[1] is a methyl or an acetyl group;
R[3] is a hydrogen atom or a methyl group;
R[4] is hydrogen and R[5] is phenylsulfphonyl, when R[3] is hydrogen; and one of R[4] or R[5] is phenylsulphonyl and the other is hydrogen, when R[3] is methyl:
and, optionally, subsequently hydrogenating the $\Delta^{15}$ double bond and, optionally, subsequently cleaving the 3 methyl ether or saponifying an acetoxy group and subsequently optionally esterifying a phenolic or tertiary hydroxy group and subsequently optionally partially saponifying a phenolic ester.

* * * * *